(12) United States Patent
Bebee (10) Patent No.: US 8,105,818 B2
(45) Date of Patent: *Jan. 31, 2012

(54) READY-TO-USE ELECTROPORATION CUVETTE INCLUDING FROZEN ELECTROCOMPETENT CELLS

(75) Inventor: Robert L. Bebee, Rockville, MD (US)

(73) Assignee: Molecular Transfer, Inc., Gaithersburg, MD (US)

( * ) Notice: Subject to any disclaimer, the term of this patent is extended or adjusted under 35 U.S.C. 154(b) by 171 days.

This patent is subject to a terminal disclaimer.

(21) Appl. No.: 11/488,179

(22) Filed: Jul. 18, 2006

(65) Prior Publication Data

US 2007/0015281 A1 Jan. 18, 2007

Related U.S. Application Data

(63) Continuation of application No. 11/072,715, filed on Mar. 7, 2005, now Pat. No. 7,078,227.

(60) Provisional application No. 60/556,380, filed on Mar. 26, 2004.

(51) Int. Cl.
*C12M 1/42* (2006.01)
*C12N 13/00* (2006.01)

(52) U.S. Cl. ............... 435/285.2; 435/173.5; 435/173.6; 435/285.1; 435/307.1

(58) Field of Classification Search ............... 435/285.2, 435/173.5, 173.6, 285.1, 307.1
See application file for complete search history.

(56) References Cited

U.S. PATENT DOCUMENTS

| 4,910,140 A | 3/1990 | Dower |
| 5,186,800 A | 2/1993 | Dower |
| 6,338,965 B1 | 1/2002 | Greener et al. |
| 2005/0282283 A1 | 12/2005 | Vozza-Brown et al. |

FOREIGN PATENT DOCUMENTS

WO  WO 03/057819  *  7/2003

OTHER PUBLICATIONS

U.S. Appl. No. 12/979,974, unpublished as of Aug. 3, 2011, Vozze-Brown, Continuation of US 2005/0282283.
Potter, "Transfection by Electroporation" in Current Protocols in Molecular Biology, Frederick M. Ausubel, et al., Copyright 2003 John Wiley & Sons, Inc.
Bio-Rad product information for Catalog No. 165-2088.

* cited by examiner

*Primary Examiner* — Maria Leavitt
(74) *Attorney, Agent, or Firm* — Perkins Coie LLP (57) ABSTRACT

A ready-to-use electroporation cuvette is provided that includes a cuvette, first and second electrodes positioned within the cuvette and electroporation competent cells frozen in a suspension solution within the cuvette, wherein the electroporation cuvette is configured to permit electroporation of the cells when the cells are thawed. The electroporation cuvette may be sealed with a cap that may be color coded to aid the user.

36 Claims, 5 Drawing Sheets

READY-TO-USE ELECTROPORATION CUVETTE INCLUDING FROZEN ELECTROCOMPETENT CELLS

This is a continuation of prior application Ser. No. 11/072,715, filed Mar. 7, 2005 now U.S. Pat. No. 7,078,227, which claims priority to 60/556,380, filed Mar. 26, 2004, the entireties of which are hereby incorporated by reference.

BACKGROUND OF THE INVENTION

1. Field of the Invention

The present invention provides an apparatus and methods for the transformation of cells by electroporation. More particularly, the invention provides a ready-to-use cuvette for electroporation and methods of making and using such a cuvette.

2. Description of the Related Art

Introducing nucleic acids into cells is central to many types of biological experiments and biotechnology development methods. For example, when searching for a gene of interest in a cDNA library, the library must be transferred into a host organism. Among the various methods used for introducing nucleic acids into host cells, electroporation has gained widespread use. Exemplary methods and kits for performing electroporation are disclosed in U.S. Pat. Nos. 4,910,140 and 5,186,800 to Dower, and 6,338,965 to Greener et al., each of which is incorporated herein by reference in their entirety.

In general, electroporation involves the transfer of nucleic acids into a host cell by exposure of the cell to a high voltage electric impulse in the presence of the nucleic acids, such as genes or gene fragments. Typically, host cells are stored by freezing them at a temperature that preserves their viability for a long term. The frozen cells are stored in a separate container and must be defrosted, mixed with nucleic acid and subsequently transferred to a cuvette prior to electroporation.

An example of an electroporation method is disclosed in U.S. Pat. No. 5,186,800 and involves growing bacteria in enriched media (of any sort) and concentrating the bacteria by washing in a buffer containing 10% glycerol. DNA is added to the cells, the DNA and cells are mixed and the resulting mixture is subjected to an electrical discharge (pulse), which temporarily disrupts the outer cell wall of the bacterial cells and permits the DNA to enter the cells.

The efficiency of nucleic acid transfer depends on a variety of factors, including the electrical field strength, the pulse decay time, the pulse shape, the temperature in which the electroporation is conducted, the type of cell, the type of suspension buffer, and the concentration and size of the nucleic acid to be transferred. Researchers have modified the host cell suspension materials to aid in freezing the cells before the electrical treatment. Methods disclosed in U.S. Pat. No. 6,338,965 include the addition of sugars or sugar derivatives, e.g., sugar alcohols, to host cells suspended in a substantially non-ionic solution, either prior to initial freezing, or after thawing, but prior to electrotransformation, which improve electroporation efficiency.

Known methods of preparing frozen cells for electroporation require thawing the cells and mixing with nucleic acid prior to adding them to a suitable electroporation cuvette. This sequence of steps has always been deemed essential for at least two reasons: first, the structures of an electroporation cuvette are precisely dimensioned in order to provide reproducible electrical field strengths in the cell solution, and the freezing procedures necessary to store cells in the cuvette were considered too harsh to maintain these precise dimensions; second, the size of the cuvette chamber was considered too small to allow efficient mixing of cells with nucleic acid. Efficient mixing of cells and nucleic acid is essential to achieving a desired level of cell transformation by electroporation. The steps of thawing and mixing host cells prior to electroporation require experimenter's time and presents an opportunity for contamination or experimental errors that may impact results or diminish electrotransformation yields. Accordingly, there is a need for a method and equipment that will eliminate the need to separately thaw and prepare cells before placing them in an electroporation cuvette.

SUMMARY OF THE INVENTION

According to an embodiment of the present invention, an electroporation cuvette includes a cuvette, first and second electrodes positioned within the cuvette, and cells in a suspension solution frozen within the cuvette, wherein the electroporation cuvette is configured to permit electroporation of the cells when the cells are thawed.

According to another embodiment of the present invention, a method of making a ready-to-use electroporation cuvette includes fabricating an electroporation cuvette comprising a cuvette, and first and second electrodes positioned within the cuvette, sterilizing the electroporation cuvette, placing an aliquot of electrocompetent cells in the electroporation cuvette, placing a sterile cap on the electroporation cuvette, and freezing the aliquot of electrocompetent cells within the electroporation cuvette, such as flash freezing, such as by dipping the cuvette in liquid nitrogen. The method may also include sealing the electroporation cuvette in a sterile package.

According to another embodiment of the present invention, a method of using a ready-to-use electroporation cuvette includes thawing cells within the electroporation cuvette, adding nucleic acid to the cells, placing the electroporation cuvette in an electroporation machine and conducting electroporation.

DETAILED DESCRIPTION OF THE EXEMPLARY EMBODIMENTS

Surprisingly it has been found that host cells, such as electrocompetent host cells, may be frozen in a suitable electroporation container, such as an electroporation cuvette according to the present invention, and then thawed, mixed with nucleic acid, and efficiently transformed by electroporation directly in the same container. This result is highly surprising because the conventional wisdom has been that containers such as electroporation cuvettes cannot withstand the rigors of the freezing procedures necessary to store competent cells, the relatively large mass of the cuvette would interfere with the rapid freezing of the cell suspension believed to be crucial to the long-term viability of the cells, and that the containers are too small to allow adequate mixing of the cells with nucleic acid after thawing. This surprising discovery permits the preparation and distribution of "ready to use" electroporation containers, such as cuvettes, that contain host cells suitable for electroporation and that permit rapid "one pot" transformation of the cells with a desired nucleic acid source.

Reference will now be made in detail to exemplary embodiments of the present invention. Wherever possible, the same reference numbers will be used throughout the drawings to refer to the same or like parts.

Figure 1:
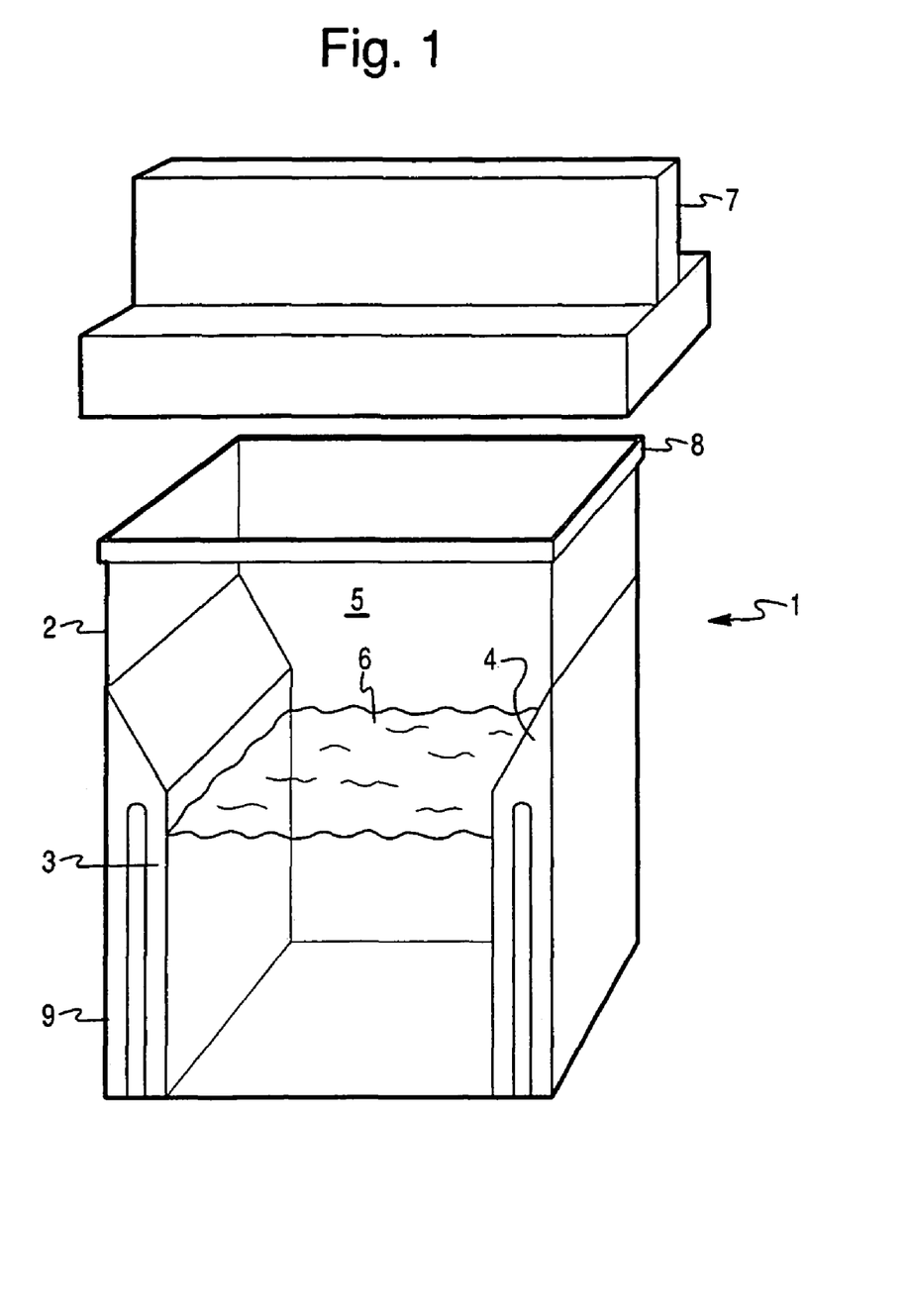
FIG. 1 is a diagram of an exemplary ready-to-use electroporation cuvette according to an embodiment of the present invention.

Referring to FIG. 1, according to an embodiment of the present invention, a ready-to-use electroporation cuvette 1 includes a vessel 2, referred to herein as a cuvette 2, containing first and second electrodes 3, 4 between which is a volume 5 in which an aliquot of cells in a suspension solution 6 are deposited and maintained in the frozen state until ready for use. The electroporation cuvette may also include a cap 7 which can be securely attached to the top of the cuvette 2.

The means for attaching the cap 7 to the cuvette 2 may be chosen from a number of structures that permit a fluid-tight and/or biologically-proof barrier, such as with a plastic deformation fit, compression fit, screw or bayonet fitting, detent structure 8 and groove fit, gasket and sealing surface fit, or similar removable closure mechanism. Alternatively or additionally, the cap may be sealed to the cuvette such as by an adhesive, shrink-wrap plastic, or glass that may be broken to remove the cap in preparation for using the cuvette.

The cuvette 2 is preferably made of a material suitable for exposure to cold temperatures, such as for example liquid nitrogen temperatures (about 77K, −196° C.), and very high voltages or electric field strengths. The cuvette material is selected to be compatible both with rapid cooling rates, such as may be experienced when the cuvette 2 is dipped into a low temperature bath (such as that used for "flash freezing" cells, for example, a liquid nitrogen bath, or a dry ice/ethanol bath), and with high voltage fields generated in the electroporation process. It is also preferable that the cuvette material be transparent. In an embodiment, the cuvette is made from a polycarbonate material, for example the polycarbonate material conventionally used for commercially available cuvettes, such as those available from, for example, Bio-Rad Laboratories (Hercules, Calif.). The cuvette 2 may be manufactured by injection molding or similar mechanism that produces a seamless structure with dimensional control over internal and external surfaces.

The electrodes 3, 4 are made of a conductive material, preferably a metal and more preferably aluminum. In an embodiment, the electrodes 3, 4 are plates that are positioned to be parallel to each other and at a fixed distance apart. In an embodiment, the internal structure of the cuvette includes structure, such as ledges or walls, that hold the electrode plates in a precise position, parallel to each other and at a fixed distance apart from top to bottom. In an alternative embodiment, the electrodes are formed so as to be self-positioning in the cuvette, such as with a wall structure 9 that can be placed against or glued to a wall of the cuvette 2, to hold the electrode surface at a precise position.

In an embodiment, electrodes 3, 4 are fabricated to be smooth in order to deliver a consistent electrical field across the entire surface, and therefore a uniform electric current through the cells. Such electrodes may be formed from aluminum plates by cleaning and then etching the surfaces to remove raised points and contaminants, rendering the electrodes smooth.

The electrodes 3, 4 may be separated by a dimension that is set to provide a predetermined electrical field through the suspension solution and cells 6 that is determined to result in a high yield of electroporation transformation of the cells. For example, cuvettes containing bacteria, such as *E. coli*, may have electrodes 3, 4 separated by about 0.1 cm to about 0.2 cm. In another example, cuvettes containing yeast may have electrodes 3, 4 separated by about 0.2 cm. In yet another example, cuvettes containing mammalian cells may have electrodes 3, 4 separated by about 0.4 cm.

Figure 2A:
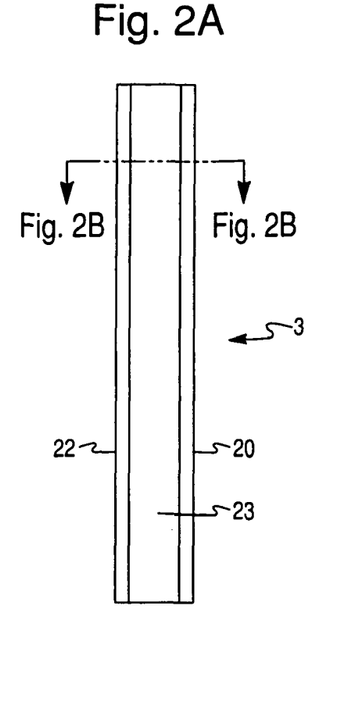
FIG. 2A is a plane view of an exemplary electrode suitable for use in a ready-to-use electroporation cuvette according to an embodiment of the present invention.
Figure 2B:
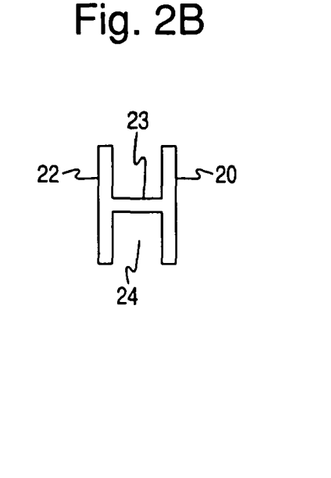
FIG. 2b is a cross-sectional diagram of the electrode illustrated in FIG. 2A.

In an embodiment, the electrodes 3 are in the form of an "I" beam as illustrated in FIGS. 2A and 2B. In this embodiment, an electrode 3 comprises a first plate 20 and a second plate 22 connected by a perpendicular interconnecting plate 23 or plates to form the "I" beam shape. As illustrated in the cross-sectional view of FIG. 2B, the interconnecting plate 23 positions the first and second plates 20, 22 a fixed distance apart. The interconnecting plate 23 also maintains the first plate 20 parallel to the second plate 22. The distance separating plates 20, 22, which forms a gap 24, is determined by the span of interconnecting plate 23. This configuration has advantages in fabrication because either the first or second plates (20 or 22) may contact the cell suspension fluid to function as the electrode surface, permitting the other surface to contact and/or be attached to a wall of the cuvette 2. If the cuvette 2 has a rectangular or square cross section, then the position and orientation of the electrode 3 in the cuvette 2 is determined by the electrode itself, in particular by the interconnecting plate 23. In this manner, a standard size cuvette (e.g., one with a square cross-section) may be used to provide electroporation cuvettes with different distances between the electrodes by using "I" beam electrodes having different spans of interconnecting plate 23. Further, the "I" beam electrodes have sufficient structural rigidity to retain their shape, and thus the controlled distance between respective electrodes, during the freezing and thawing processes.

Returning to FIG. 1, the cap 7 may be made by injection molding of a similar or different material as the cuvette. In a preferred embodiment the cap may be color coded or otherwise marked to indicate the type of cells contained in the cuvette and/or the dimension separating the electrodes 3, 4, since such information is useful to users of the ready-to-use cuvette. The color coding permits the user to easily select the proper cuvette for a particular experiment by observing the cap, which is advantageous when a number of cuvettes are stored together in a freezer.

Figure 3:
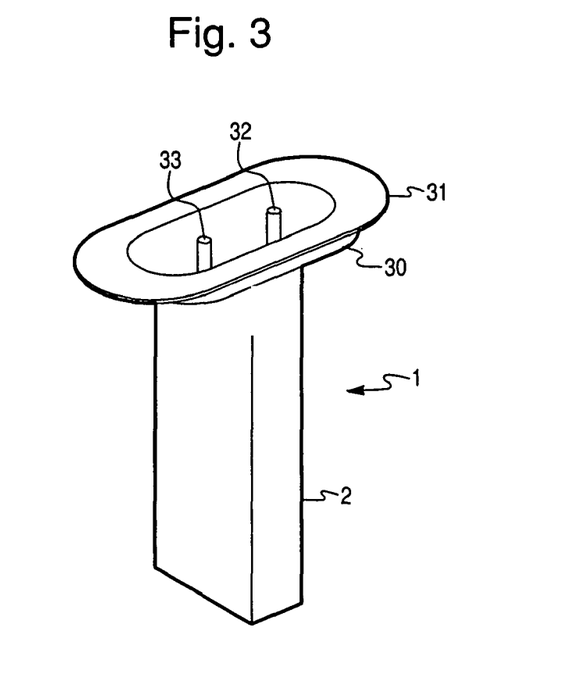
FIG. 3 is a diagram of a ready-to-use electroporation cuvette according to another embodiment of the present invention.

Alternative configurations of the cuvette are contemplated. FIG. 3 illustrates an alternative embodiment featuring structures to permit positioning within an electroporation machine. For example, the cuvette 1 may include a seating ledge 30 that may interface with a complementary structure on the electroporation machine. Also, the cuvette 1 may include a handling structure or flange 31 to permit easy handling of the cuvette 1 without conducting heat into the cells or risking contamination of the interior. The cuvette 1 may also include electrical connections 32, 33 for ease of connecting the electrodes (not shown in FIG. 3) to the electroporation machine.

Figure 4:
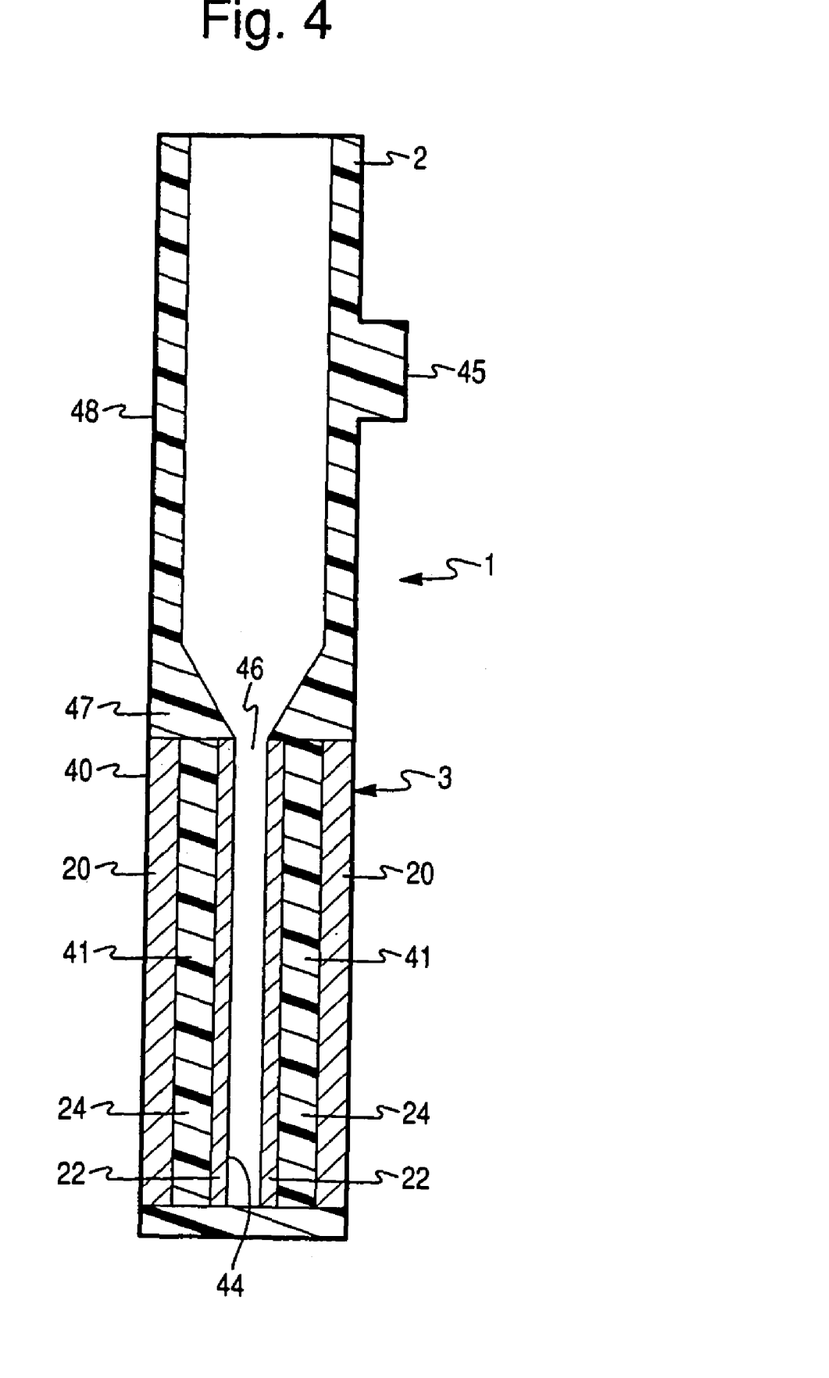
FIG. 4 is a plane view of a ready-to-use electroporation cuvette according to another embodiment of the present invention.

In another alternative embodiment illustrated in FIG. 4, the electroporation cuvette 1 may be formed by fusing the cuvette 2 with "I" beam electrodes 3. In this embodiment, two walls 41 of the cuvette, 2 pass through the gap 24 (see FIG. 2B) in the "I" beam so that one of the electrode plates 20 forms a portion of the exterior to the cuvette 2, permitting that plate 20 to serve as an electrical contact surface 40 for interfacing electrically with the electroporation machine. On the inside, the other electrode plate 22 forms a portion of the interior of the cuvette 2, where it functions as the electrode surface 44. In this embodiment, the interconnecting plate 23 (FIG. 2B) conducts electricity between the exterior facing plate 20 and the interior face plate 22. The exterior surface of the cuvette 2 may also feature position-orienting structures, such as a tab 45, that interfaces with a corresponding structure in the electroporation machine to ensure the cuvette is inserted in a proper orientation. The cuvette 2 may also feature structures to strengthen the assembly and to facilitate flow of liquids into the gap 46 between electrode surfaces 44, such as a wedge-shaped blend 47 between the upper wall 48 of the cuvette 2 and the electrode surface 44. As described above with respect to FIG. 2A, 2B, the size of the gap 46 in the cuvette 2 may be varied by changing the span of the interconnecting plate 23 (FIG. 2B), varying the gap 24 between plates 20, and 22 of each electrode, without varying the outside dimensions of the cuvette 2.

Figure 5:
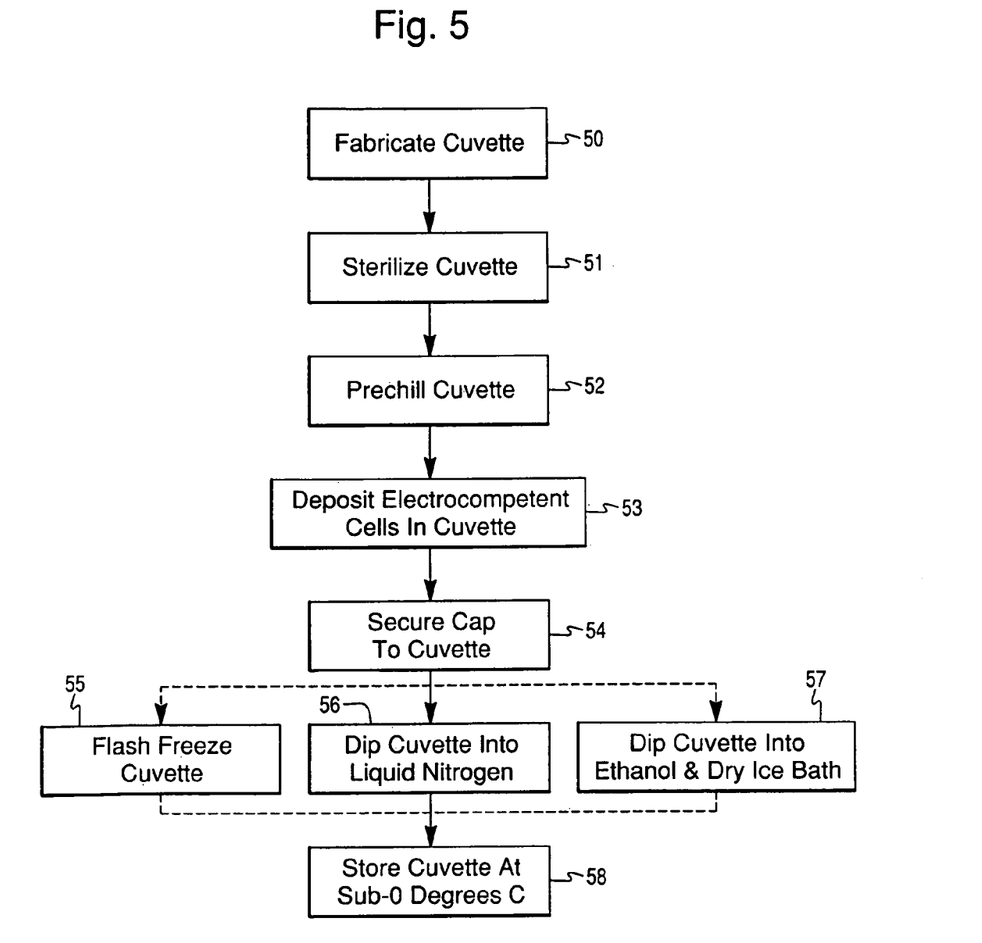
FIG. 5 is a process flow diagram for making an electroporation cuvette according to an embodiment of the present invention.

Manufacture and assembly of the ready-to-use cuvette is summarized in FIG. 5. The cuvette is fabricated by a suitable method, such as injection molding, and electrodes are positioned in the cuvette, which may be accomplished by fusing the electrodes into the cuvette, or gluing or force-fitting the electrodes into electrode positioning structure. Step 50. The cuvette may thus be designed and manufactured for a single use. An example of a suitable cuvette is the Gene Pulser® Cuvette, Catalog No. 165-2089 manufactured by Bio-Rad Laboratories of Hercules, Calif.

Once assembled, the cuvette is sterilized, step 51. Sterilization may include one or more of chemical cleaning, heat treatment and exposure to gamma or X-ray radiation, or other suitable sterilization process.

The cuvette may then be prechilled, such as by suspending it in a water ice bath, in preparation for depositing cells into the cuvette. Step 54.

Cells for electroporation are added to a suitable suspension solution, and then an aliquot of cells and solution are added to the chilled cuvette. Step 54. The cells may be any cells suitable for electroporation, including for example, bacteria such as *E. coli*, yeast, plant or mammalian cells. The cells may be treated to render them competent for electroporation, which may include using a suspension solution that renders the cells electroporation competent. Suitable suspension solutions are well known in the art.

Once cells and suspension solution have been added, the cuvette is sealed with a cap providing a sterile barrier to prevent contamination. Step 54. Cells and suspension solution are then rapidly frozen, such as by flash freezing, step 55, dipping or submerging the cuvette in liquid nitrogen, step 56, dipping or submerging the cuvette in a bath of ethanol and dry ice, step 57, or placing the cuvette in a freezer, such as a freezer at about −85° C. or a rate-controlled freezer. In various embodiments of the present invention, the cap may be attached to the cuvette before or after freezing.

Once the cells and suspension solution have been frozen, the cuvette is stored in a freezer or other suitable cold storage means until ready for use. Step 58. By maintaining the cuvette below 0° C., such as in ultra-cold storage at about −78° C., the cells may be maintained ready for use for an extended period of time.

Figure 6:
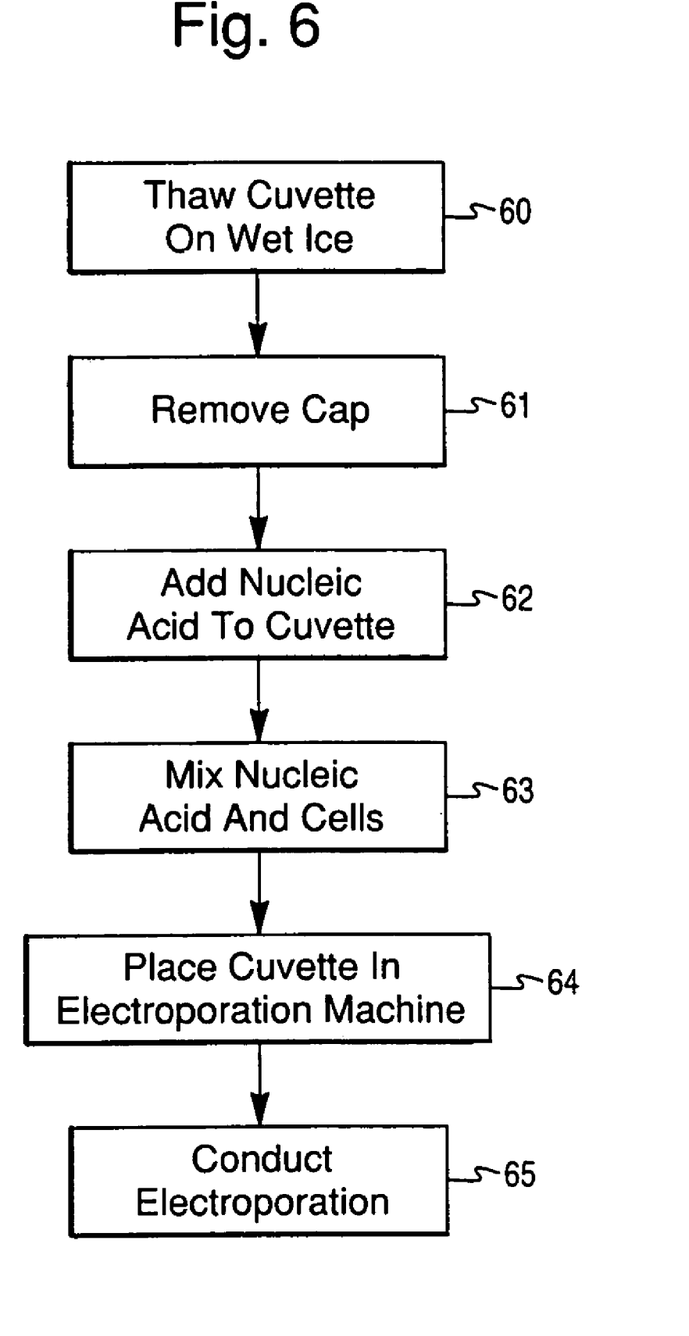
FIG. 6 is a process flow diagram for using an electroporation cuvette according to an embodiment of the present invention.

Use of the ready-to-use cuvette is illustrated in FIG. 6. Once the appropriate cuvette is selected, such as based upon the color code on the cap, the cells and suspension solution are gently thawed, such as by placing the cuvette on wet ice. Step 60. Once thawed, the cap is removed, step 61, and a suitable amount of a nucleic acid, such as in a suspension solution, is added by a user. Step 62. The nucleic acid is mixed with the cells and suspension solution. Step 63. A suitable method of mixing nucleic acid and cells/suspension solution within the electroporation cuvette comprises alternately drawing solution up into a micropipette and expelling the solution down into the cuvette a number of times, such as 3 or 4 times, followed by rapping the cuvette on a solid surface, such as a laboratory bench.

Once the nucleic acid and cells/suspension have been mixed, the cuvette may be placed in a suitable electroporation machine, step 64, and electroporation conducted, step 65. Electroporation machines and methods for using them to conduct electroporation transformation of cells are well known in the art.

Following electroporation, the cells are placed on or in an appropriate medium to promote growth of the transformed cells. The chosen medium should propagate the transformed cells that either transiently express or have nucleic acids integrated into the host cells' genome. Further, the medium advantageously should be selected so as to assist the cells in recovering from the electrical treatment.

Suitable cell suspension solutions are substantially non-ionic solutions in order to ensure a predictable electric current is produced in the cells. An appropriate non-ionic solution may be a buffer solution with minimal or no ions present. Non-ionic solutions may also be non-polar. The concentration of ions in the buffer is adequately low so that when electricity is discharged into the host cells, little or no additional current is carried into the cells. The presence of ions in the buffer may result in additional current being carried into the cells and can lower the survival rate of the host cells. In some embodiments of the invention, the non-ionic solution includes glycerol at about 5% to about 10% solution or dimethyl sulfoxide from about 2% to about 15% solution, depending upon the application.

The solution may also comprise at least one sugar or sugar derivative, such as D-stereoisomeric or the L-forms (enantiomers) form. The concentration of the sugar or derivative may be about 2.0% to about 2.5%. In specific embodiments, the added sugar derivative is sorbitol and its concentration is about 2.5%. Specific sugars may include, but are not limited to: aldoses, such as monosaccharides which include trioses (i.e. glyceraldehyde), tetroses (i.e. erythrose, threose), pentoses (i.e. arabinose, xylose, ribose, lyxose), hexoses (i.e. glucose, mannose, galactose, idose, gulose, altrose; allose, talose), heptoses (i.e. sedoheptulose), octoses (i.e. glycero-D-manno-octulose), pentose ring sugars (i.e. ribofuranose, ribopyranose); disaccharides (i.e., sucrose, lactose, trehalose, maltose, cellobiose, gentiobiose); and trisaccharides (i.e., raffinose), oligosaccharides (i.e., amylose, amylopectin, glycogen).

Sugar derivatives that may be used include, but are not limited to: alditols or aldose alcohol, which include erythritol, glucitol, sorbitol, or mannitol; ketoses, e.g., dihydroxyacetone, erythrulose, ribulose, xylulose, psicose, fructose, sorbose, and tagatose; aminosugars such as glucosamine, galactosamine, N-acetylglucosamine, N-acetylgalactosamine, muramic acid, N-acetyl muramic acid, and N-acetyineuraminic acid (sialic acid); glycosides, such as glucopyranose and methyl-glucopyranose; and lactones, such as gluconolactone.

Nucleic acids that may be added to the ready-to-use electroporation cuvette may include, but are not limited to, RNA, DNA, or non-naturally occurring nucleic acid sequences that encode functional or non-functional proteins, and fragments of those sequences, polynucleotides, or oligonucleotides. The nucleic acids of interest may be obtained naturally or synthetically, e.g., using PCR or mutagenesis. Further, the nucleic acids may be circular, linear, or supercoiled in their topology. Preferably, the nucleic acids may range from about 3 kb to about 300 kb.

EXAMPLES

Preparation of Ready-To-Use Electroporation Cuvettes. A recA-minus derivative of *E. coli* strain MC1061 was inoculated into 1 liter of SOB (minus magnesium) growth medium and incubated at 37° C. and 275 rpm overnight (approximately 15 hours). The overnight culture was diluted 1:50 into 1.5 liters of SOB (minus magnesium) and grown at 39° C., 275 rpm until an OD550 of 1.0 was reached. Cells were harvested by centrifugation and then washed by resuspending in an equal (to the original) volume of cold (approx. 4° C.) 10% glycerol. The washing step was repeated one time. The final cell pellet was resuspended in a minimal amount of 10% glycerol. The final concentration of the cells was adjusted to ~250 OD550 units/ml with cold 10% glycerol. The cell suspension was dispensed in 20 µl aliquots into pre-chilled electroporation cuvettes (Gene Pulser® Cuvette from Bio-Rad Laboratories), flash-frozen by partial immersion of the cuvettes in liquid nitrogen, and then stored in an ultra-cold freezer at about −75° C.

Use of Ready-To-Use Electroporation Cuvettes in Transformation: The cuvettes prepared according to the procedure described above were removed from the freezer and placed on ice for about 10 minutes to thaw the cells. One microliter of pUC19 (10 pg) nucleic acid was pipetted directly into the thawed cells and the material was mixed with the cells in the cuvette by pipetting the combined solution up and down several times. Further mixing of the material was achieved by rapping the cuvette sharply on the bench top several times. The mixture was then subjected to electroshock using a Bio-Rad Micropulser from Bio-Rad Laboratories on pre-programmed setting of "Ec1". Immediately after pulsing, the cells were removed from the cuvette by rinsing out the electrode gap with 980 µl of SOC, and transferring the resulting liquid to sterile snap-cap polypropylene tubes (Falcon 2059). The tubes were shaken at 275 rpm, 37° C. for about 1 hour. The liquid was then diluted 1:100, and 100 µl of this dilution was plated onto LB+100 µg/ml ampicillin plates and incubated overnight at 37° C.

The foregoing description of various embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated.

What is claimed is:

1. A method of using an electroporation cuvette containing a frozen, ready-to-use aliquot of electrocompetent cells, comprising:

thawing the aliquot of electrocompetent cells within the electroporation cuvette;

mixing the thawed cells with a composition comprising a nucleic acid;

placing the electroporation cuvette in an electroporation machine;

delivering an electrical pulse to the electrocompetent cells, thereby transforming said electrocompetent cells with the nucleic acid, wherein said electroporation cuvette is an electroporation cuvette comprising:

first and second electrodes positioned within the electroporation cuvette; and cells frozen within the electroporation cuvette, wherein the electroporation cuvette is configured to permit electroporation of the cells when the cells are thawed, and wherein the cuvette is configured to position said first and second electrodes at a predetermined distance apart during electroporation.

2. The method of claim 1, wherein the electroporation cuvette further comprises a cap removably secured to the electroporation cuvette and further comprising the step of removing the cap.

3. The method of claim 1, wherein the electroporation cuvette is made of a polycarbonate material.

4. The method of claim 1, wherein the electroporation cuvette cap is color-coded to identify the predetermined distance separating the first and second electrodes, and further comprising selecting an electroporation cuvette based upon the color code on the cap.

5. The method of claim 1, wherein the electrocompetent cells are bacteria.

6. The method of claim 5, wherein the electrocompetent cells are *E. coli*.

7. The method of claim 1, wherein the electrocompetent cells are a yeast.

8. The method of claim 1, wherein the electrocompetent cells are mammalian.

9. The method of claim 2, wherein the step of thawing the aliquot of electrocompetent cells within the electroporation cuvette is performed before the step of removing the cap.

10. The method of claim 9, wherein the step of thawing the aliquot of electrocompetent cells comprises placing the electroporation cuvette on wet ice.

11. The method of claim 1, wherein the step of mixing comprises pipetting the thawed cells and composition up and down.

12. The method of claim 11, wherein the step of mixing further comprises tapping the electroporation cuvette.

13. A method of manufacturing a ready-to-use electroporation cuvette, comprising:

sterilizing an electroporation cuvette comprising first and second electrodes positioned within the electroporation cuvette; and cells frozen within the electroporation cuvette, wherein the electroporation cuvette is configured to permit electroporation of the cells when the cells are thawed, and wherein the cuvette is configured to position said first and second electrodes at a predetermined distance apart during electroporation;

placing an aliquot of electrocompetent cells in the electroporation cuvette;

placing a sterile cap on the electroporation cuvette; and freezing the aliquot of electrocompetent cells within the electroporation cuvette.

14. The method of manufacture according to claim 13, further comprising sealing the electroporation cuvette in a sterile package.

15. The method of manufacture according to claim 13, wherein the step of freezing the aliquot of electrocompetent cells is accomplished by flash freezing.

16. The method of manufacture according to claim 13, wherein the step of freezing the aliquot of electrocompetent cells comprises at least partially submerging the electroporation cuvette in liquid nitrogen.

17. The method of manufacture according to claim 13, wherein the step of freezing the aliquot of electrocompetent cells is accomplished using a freezer.

18. The method of manufacture according to claim 13, wherein the step of freezing the aliquot of electrocompetent cells comprises at least partially submerging the electroporation cuvette in an ethanol and dry ice bath.

19. A method of using an electroporation cuvette containing a frozen, ready-to-use aliquot of electrocompetent cells, comprising:
  a) thawing the aliquot of electrocompetent cells within the electroporation cuvette;
  b) mixing the thawed cells with a composition comprising a nucleic acid;
  c) placing the electroporation cuvette in an electroporation machine;
  d) delivering an electrical pulse to the electrocompetent cells, thereby transforming said electrocompetent cells with the nucleic acid, wherein said electroporation cuvette is an electroporation cuvette comprising:
  first and second electrodes positioned within the electroporation cuvette; and cells frozen within the electroporation cuvette, wherein the electroporation cuvette is configured to permit electroporation of the cells when the cells are thawed, and
  wherein the cuvette is configured to position said first electrode parallel to said second electrode.

20. The method of claim 19, wherein the electroporation cuvette further comprises a cap removably secured to the electroporation cuvette and further comprising the step of removing the cap.

21. The method of claim 19, wherein the electroporation cuvette is made of a polycarbonate material.

22. The method of claim 19, wherein the electroporation cuvette cap is color-coded to identify the predetermined distance separating the first and second electrodes, and further comprising selecting an electroporation cuvette based upon the color code on the cap.

23. The method of claim 19, wherein the electrocompetent cells are bacteria.

24. The method of claim 23, wherein the electrocompetent cells are *E. coli*.

25. The method of claim 19, wherein the electrocompetent cells are a yeast.

26. The method of claim 19, wherein the electrocompetent cells are mammalian.

27. The method of claim 20, wherein the step of thawing the aliquot of electrocompetent cells within the electroporation cuvette is performed before the step of removing the cap.

28. The method of claim 27, wherein the step of thawing the aliquot of electrocompetent cells comprises placing the electroporation cuvette on wet ice.

29. The method of claim 19, wherein the step of mixing comprises pipetting the thawed cells and composition up and down.

30. The method of claim 29, wherein the step of mixing further comprises tapping the electroporation cuvette.

31. A method of manufacturing a ready-to-use electroporation cuvette, comprising
  a) sterilizing an electroporation cuvette comprising first and second electrodes positioned within the electroporation cuvette; subsequently
  b) placing an aliquot of electrocompetent cells in the electroporation cuvette;
  c) placing a sterile cap on the electroporation cuvette; and
  d) freezing the aliquot of electrocompetent cells within the electroporation cuvette;
  wherein the electroporation cuvette is configured to permit electroporation of the cells when the cells are thawed, and wherein the electroporation cuvette is configured to position said first and second electrodes at a predetermined distance apart during electroporation.

32. The method of manufacture according to claim 31, further comprising sealing the electroporation cuvette in a sterile package.

33. The method of manufacture according to claim 31, wherein the step of freezing the aliquot of electrocompetent cells is accomplished by flash freezing.

34. The method of manufacture according to claim 31, wherein the step of freezing the aliquot of electrocompetent cells comprises at least partially submerging the electroporation cuvette in liquid nitrogen.

35. The method of manufacture according to claim 31, wherein the step of freezing the aliquot of electrocompetent cells is accomplished using a freezer.

36. The method of manufacture according to claim 31, wherein the step of freezing the aliquot of electrocompetent cells comprises at least partially submerging the electroporation cuvette in an ethanol and dry ice bath.

* * * * *